United States Patent [19]
Hatori

[11] Patent Number: 5,066,126
[45] Date of Patent: Nov. 19, 1991

[54] OPTICAL SPECTRUM ANALYZER

[75] Inventor: Masami Hatori, Kanagawa, Japan

[73] Assignee: Fuji Photo Film Co., Ltd., Kanagawa, Japan

[21] Appl. No.: 385,746

[22] Filed: Jul. 18, 1989

[30] Foreign Application Priority Data

Jul. 19, 1988 [JP] Japan .................. 63-179648

[51] Int. Cl.$^5$ .............. G01J 3/28; G01J 3/06; G02B 6/10
[52] U.S. Cl. .................... 356/328; 356/308; 385/1; 385/7
[58] Field of Search ............ 356/308, 328, 345, 346, 356/73; 250/339; 350/96.13

[56] References Cited

U.S. PATENT DOCUMENTS

| | | | |
|---|---|---|---|
| 3,012,467 | 12/1961 | Rosenthal | 356/308 |
| 4,297,704 | 10/1981 | Marom et al. | 350/96.13 |
| 4,736,103 | 4/1988 | Nelson et al. | 250/339 |
| 4,834,535 | 5/1989 | Cammann | 356/308 |
| 4,883,963 | 11/1989 | Kennedy et al. | 250/339 |
| 4,900,113 | 2/1990 | Hatori | 356/302 |

Primary Examiner—Vincent P. McGraw
Assistant Examiner—LaCharles P. Keesee
Attorney, Agent, or Firm—Sughrue, Mion, Zinn, Macpeak & Seas

[57] ABSTRACT

An optical spectrum analyzer includes a surface elastic wave generator for generating in an optical waveguide a surface elastic wave which has a continuously varying frequency and which diffracts and deflects a guided wave as it travels across the path of the guided wave, which guided wave is introduced as a measured light beam into and travels in the optical wave guide. The measured light beam which has been deflected is emitted from the optical waveguide and detected by a light detector. A modulator turns on and off or modulates the surface elastic wave by repeatedly energizing and de-energizing the surface elastic wave generator, the frequency of the modulation being lower than the continuously varying frequency. A filter receives a signal corresponding to the modulation frequency from the modulator and a signal corresponding to the measured light beam from the detector, and extracts a signal component having the same frequency as the modulation frequency from the signal received from the light detector. The frequency of the surface elastic wave is detected on the basis of the signal component extracted by the filler when the measured light beam is detected by the light detector.

4 Claims, 4 Drawing Sheets

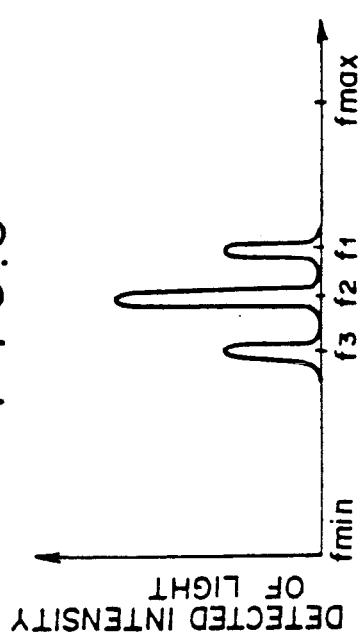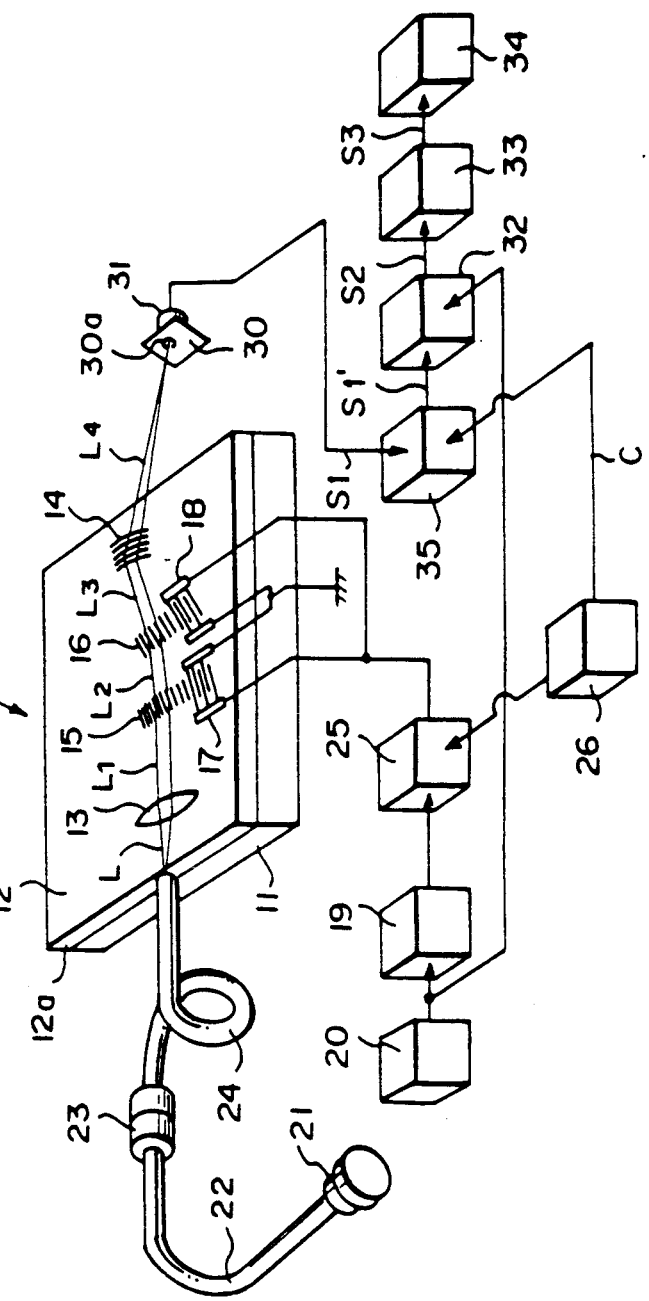

OPTICAL SPECTRUM ANALYZER

BACKGROUND OF THE INVENTION

1. Field of the Invention

The present invention relates to an optical spectrum analyzer for analyzing an optical spectrum, i.e., measuring the magnitude of signal components of the spectrum over a certain frequency range, and more particularly to an optical spectrum analyzer, the operation of which is based on an acoustooptic effect.

Various spectrum analyzers for analyzing optical spectrum are known in the art. One conventional optical spectrum analyzer that has widely been used in practice is the Czerny-Turner optical spectrum analyzer. This optical spectrum analyzer operates as follows: A diffraction grating which diffracts a light beam applied to the optical spectrum analyzer is rotated thereby to move the diffracted light over a slit. The spectrum of the light is analyzed on the basis of the angle through which the diffraction grating has been rotated when the diffracted light is detected through the slit. An optical spectrum analyzer of this type can analyze optical spectrums with high resolution.

However, Czerny-Turner optical spectrum analyzers cannot be handled with ease because they are large and heavy, and hence are not portable. Smaller and lighter optical spectrum analyzers have also been proposed, but they have a poor resolution.

SUMMARY OF THE INVENTION

It is an object of the present invention to provide an optical spectrum analyzer which is small and lightweight, but can analyze optical spectrums with high resolution.

According to the present invention, there is provided an optical spectrum analyzer comprising an optical waveguide made of a material capable of propagating a surface elastic wave therethrough, surface elastic wave generating means for generating in the optical waveguide a surface elastic wave which has a continuously varying frequency and which diffracts and deflects a guided wave by traveling across its path, which guided wave is introduced as a measured light beam into and travels in the optical waveguide, light detecting means for detecting a measured light beam which has been deflected by the surface elastic wave and emitted from the optical waveguide, modulating means for turning on and off the surface elastic wave by repeatedly energizing and de-energizing the surface elastic wave generating means, the frequency of the modulation being lower than the continuously varying frequency, filter means for receiving a signal representing the modulation frequency from the modulating means and a signal corresponding to the measured light beam from the light detecting means, and for extracting a signal component having the same frequency as the modulation frequency from the signal received from the light detecting means, and frequency detecting means which is responsive to the signal component extracted by the filter means and detects the frequency of the surface elastic wave when the measured light beam is detected by the light detecting means.

When the guided wave traveling through the optical waveguide and the surface elastic wave propagated through the optical waveguide intersect with each other, the guided wave is diffracted and deflected by an acoustooptic interaction between itself and the surface elastic wave. The angle $\delta$ through which the guided wave is deflected is $\delta = 2\theta$ where $\theta$ is the angle of incidence of the guided wave with respect to the direction in which the surface elastic wave travels. The angle $2\theta$ is expressed as follows:

$$2\theta = 2\sin^{-1} \frac{\lambda}{2Ne \cdot \Lambda} \quad (1)$$
$$= 2\sin^{-1} \frac{\lambda \cdot f}{2Ne \cdot v}$$

where $\lambda$ is the wavelength of the guided wave, Ne is the effective refractive index of the optical waveguide with respect to the guided wave, and $\Lambda$, f, v are the wavelength, frequency, and speed, respectively, of the surface elastic wave. Since Ne and v are constant, the wavelength $\lambda$ of the guided wave or the measured light beam can be determined if the angle $\theta$ of incidence and the frequency f of the surface elastic wave are known when the conditions for Bragg diffraction indicated by equation (1) are satisfied and hence the guided wave is diffracted most efficiently.

If the guided wave or the measured light beam contains a plurality of spectral components having wavelengths which lie very close to each other, these spectral components can be separated from each other by the diffracting action of the surface elastic wave. A pinhole plate or the like may be positioned in front of the light detecting means so that light beams representing the spectral components can individually be detected through the pinhole plate by the light detecting means. The spectral components can thus be measured accurately even if their wavelengths lie close to each other.

When the surface elastic wave is modulated or turned on and off, the guided wave diffracted by the surface elastic wave is modulated or turned on and off at the same frequency as the frequency of the modulation. A signal component having the same frequency as the modulation frequency is extracted from the output signal of the light detecting means. The extracted signal component is based substantially solely on the guided wave or the measured light beam. Even if the output signal from the light detecting means contains noise, since the noise is removed, the measured light beam is detected with a high signal-to-noise ratio.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 5 is a graph showing the relationship between the detected intensities of light beams and the frequency of a surface elastic wave in the optical spectrum analyzer shown in FIG. 1, FIG. 6 is a schematic perspective view, partly in block form, of an optical spectrum analyzer according to a second embodiment of the present invention.

DESCRIPTION OF THE PREFERRED EMBODIMENTS

Figure 1:
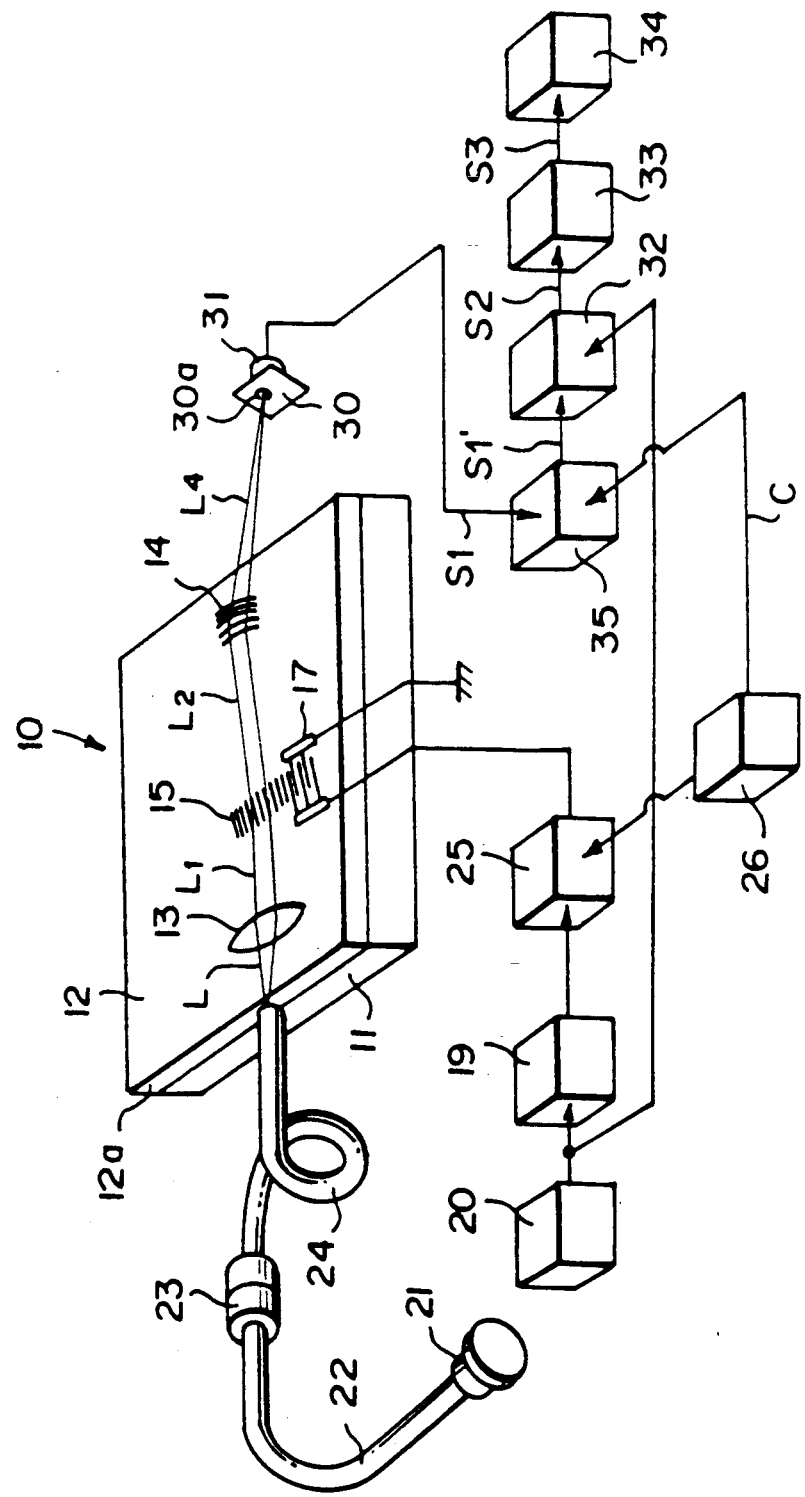
FIG. 1 is a schematic perspective view, partly in block form, of an optical spectrum analyzer according to a first embodiment of the present invention.

FIG. 1 shows an optical spectrum analyzer in accordance with a first embodiment of the present invention. The optical spectrum analyzer, generally designated by the reference numeral 10, includes a substrate 11, an optical waveguide 12 formed on the substrate 11, a waveguide lens 13 formed in the optical waveguide 12, a focusing grating coupler (FGC) 14 which emits a light beam, and a chirped interdigital transducer (IDT) 17 which is formed in the optical waveguide 12 and generates a surface elastic wave 15 which travels across the path of a guided wave propagated through the optical waveguide 12 from the waveguide lens 13 toward the FGC 14. The optical spectrum analyzer 10 further includes a high-frequency amplifier 19 which applies a high-frequency AC voltage to the chirped IDT 17 to enable the chirped IDT 17 to generate the surface elastic wave 15, a sweeper 20 which continuously varies or sweeps the frequency of the AC voltage, a switching circuit 25 which is connected between the chirped IDT 17 and the high-frequency amplifier 19 and turns the AC voltage applied to the IDT 17 on and off, and a modulation control circuit 26 which controls the operation of the switching circuit 25.

The FGC 14 emits a light beam $L_4$ toward a pinhole plate 30. A light detector 31, which comprises a photodiode or the like and is used to measure the intensity of the light beam $L_4$, is positioned behind the pinhole plate 30. The light detector 31 produces a light intensity signal S1 which is amplified by a lock-in amplifier 35. The lock-in amplifier 35 applies an output signal S1' to a sampling circuit 32 whose frequency-detected output signal S2 is supplied to a control circuit 33.

In this embodiment, the substrate 11 is in the form of a wafer of $LiNbO_3$, for example, and a Ti-diffused film, for example, is provided on the surface of the wafer and forms the optical waveguide 12. However, the substrate 11 may be a crystalline substrate of sapphire, Si, or the like, and the optical waveguide 12 may comprise a film of any other suitable material formed by sputtering, evaporation, or the like. Optical waveguides are described in detail in *Integrated Optics* edited by T. Tamir, Topics in Applied Physics, Vol. 7, published by Springer-Verlag, 1975, and *Optical Integrated Circuits* written by Nishihara, Haruna, and Suhara, and published by Ohm Co., 1985. The optical waveguide 12 of the present invention may be any of the known optical waveguides. However, the optical waveguide 12 should be made of a material such as a Ti-diffused film capable of propagating a surface elastic wave. The optical waveguide 12 may be of a laminated structure of two or more films or layers.

The chirped IDT 17 may be formed as follows, for example: a positive electron beam resist is coated on the surface of the optical waveguide 12; an electrically conductive thin film of Au is evaporated onto the positive electron beam resist; an electrode pattern is then printed with an electron beam on the thin film of Au; the thin film of Au is peeled off; thereafter the electrode pattern is developed; then thin films of Cr and Al are evaporated on the surface formed thus far and the unnecessary layers are lifted off in an organic solution. If the substrate 11 and the optical waveguide 12 are made of a piezoelectric material, then the chirped IDT 17 which generates the surface elastic wave 15 may directly be disposed in the optical waveguide 12 or on the substrate 11. If the substrate 11 and the optical waveguide 12 are not made of a piezoelectric material, then a piezoelectric thin film of ZnO, for example, is deposited on a portion of the substrate 11 or the optical waveguide 12 by evaporation, sputtering, or the like, and then the IDT 17 is formed on the piezoelectric thin film.

A light beam L to be subjected to spectrum analysis is emitted from a light source 21 such as a semiconductor laser. The emitted light beam L travels through an optical fiber 22 coupled to the light source 21, a coupler 23, and an optical fiber 24 directly coupled to an end face 12a of the optical waveguide 12. The light beam L then enters the optical waveguide 12 at the end face 12a. The light beam L (divergent beam) is converged by the waveguide lens 13 into a parallel beam which is then introduced into the optical waveguide 12 and travels as a guided wave $L_1$ in the optical waveguide 12. If the conditions for Bragg diffraction which are represented by equation (1) above are met, the guided wave $L_1$ is then diffracted (through Bragg diffraction) into a guided wave $L_2$ due to an acoustooptic interaction between itself and the surface elastic wave 15 produced by the chirped IDT 17. The diffracted guided wave $L_2$ is then emitted as the light beam $L_4$ out of the optical waveguide 12 by the FGC 14, and focused into a spot by the beam converging action of the FGC 14.

Figure 2:
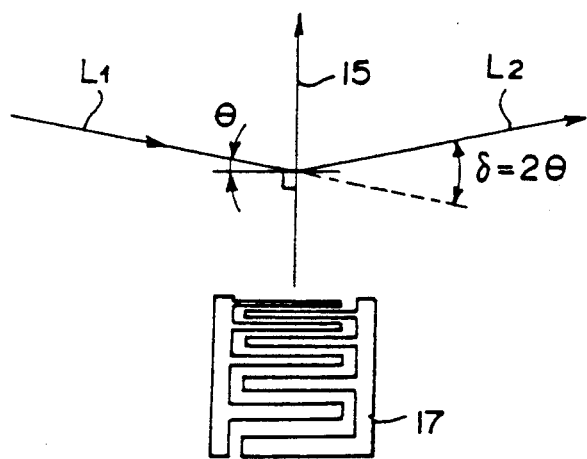
FIG. 2 is an enlarged plan view of a portion of the optical spectrum analyzer shown in FIG. 1.
Figure 3:
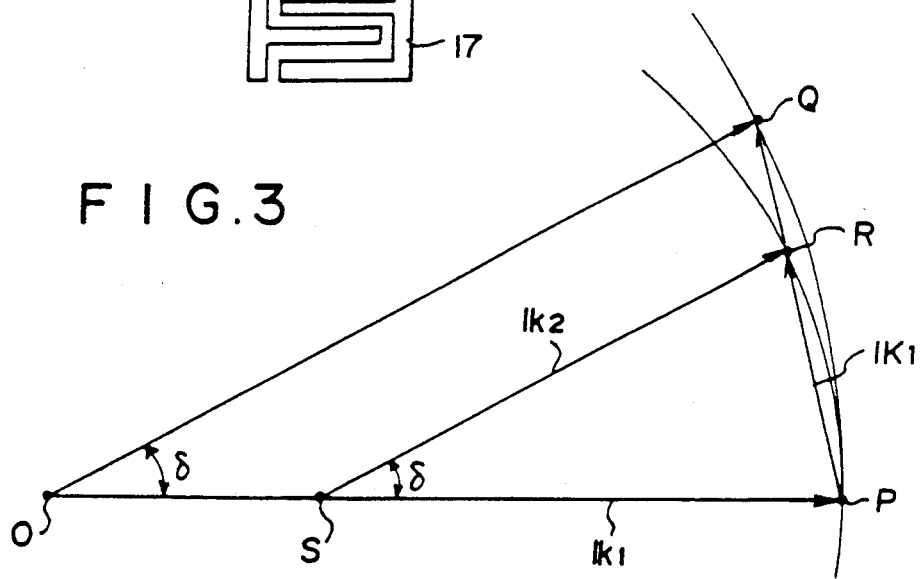
FIG. 3 is a diagram showing the manner in which an optical beam is deflected in the optical spectrum analyzer shown in FIG. 1.

The deflection and diffraction of the guided wave will be described below with reference to FIGS. 2 and 3. FIG. 2 shows the chirped IDT 17 on an enlarged scale, and FIG. 3 shows wave vectors of the guided wave $L_1$ and the surface elastic wave 15. As shown in FIG. 2, the guided wave $L_1$ is applied at a constant angle of $\theta$ with respect to the direction in which the surface elastic wave 15 travels. More specifically, if it is assumed that the guided wave $L_1$ has a wave vector $k_1$, the diffracted guided wave $L_2$ a wave vector $k_2$, and the surface elastic wave 15 a wave vector $K_1$, then as shown in FIG. 3, the following relationship is met:

$$k_1 + K_1 = k_2 \qquad (2)$$

when the Bragg conditions for diffraction as represented by equation (1) are met. The angle through which the guided wave $L_2$ has been deflected with respect to the guided wave $L_1$ is $\delta = 2\theta$. If the angle $\theta$ of incidence is constant as described above, then the angle $\delta$ of deflection when equation (2) is satisfied is also constant. Therefore, the light beam $L_4$ which fully satisfies the Bragg conditions for diffraction is always traveling in the same direction when it is emitted from the optical waveguide. The pinhole plate 30 placed in front of the light detector 31 is positioned such that the light beam $L_4$ which is always emitted in the same direction from the optical waveguide passes through a pinhole 30a defined in the pinhole plate 30.

It is assumed that the guided wave $L_1$ (the light beam to be measured) has a wavelength $\lambda$ and the surface elastic wave 15 has a wavelength $\Lambda$. Since $|k_1| = 2\pi/\lambda$, and the guided wave $L_2$ also has a wavelength $\lambda$, we get:

$$|k_1| = |k_2| = 2\pi/\lambda$$

Therefore, insofar as the angle $\theta$ of incidence is fixed, there is only one value of $|k_1| = 2\pi/\lambda$ which meets equation (2) above with respect to one $|k_1|$. The wavelength $\lambda$ can then be determined from the value of $|K_1|$ at the time equation (2) is satisfied (i.e., when the light beam $L_4$ passes through the pinhole $30a$ and is detected by the light detector 31), i.e., from the value of the wavelength $\lambda$ of the surface elastic wave 15.

It is also possible to determine the wavelength $\lambda$ from equation (1) above. The wavelength $\lambda$ can be found even if the angle $\theta$ of incidence and the refractive index Ne of the optical waveguide 12 with respect to the guided wave $L_1$ are unknown. More specifically, a reference wave having a known wavelength $\lambda$ref is introduced into the optical waveguide 12, and diffracted by a reference surface elastic wave having a wavelength $\Lambda$. If, as in FIG. 3, the reference wave has a wave vector $\vec{OP}$, the reference surface elastic wave a wave vector $\vec{PQ}$, and the diffracted reference wave a wave vector $\vec{OQ}$, then since $\triangle OPQ - \triangle SPR$, we get:

$$\frac{|k|}{OP} = \frac{|K|}{PQ}$$

Because $OP = 2\pi/\lambda\text{ref}$, $PQ = 2\pi/\lambda\text{ref}$, we get:

$$\lambda = \lambda\text{ref}(\Lambda/\Lambda\text{ref})$$

If it is assumed that the surface elastic wave 15 has a speed v and a frequency f and the reference surface elastic wave has a speed vref and a frequency fref, then $v = f\Lambda$, $v\text{ref} = f\text{ref} \cdot \Lambda\text{ref}$, and $v = v\text{ref}$. Consequently, the following equation is derived from the above equation:

$$\lambda = \lambda\text{ref}(f\text{ref}/f) \qquad (3)$$

The wavelength $\lambda$ of the measured light beam can thus be determined according to equation (3) if the wavelength $\lambda$ref of the reference wave and the frequency fref of the reference surface elastic wave are known.

The frequency of the high-frequency AC voltage applied to the chirped IDT 17 for optical spectrum analysis is continuously swept from fmin to fmax by the sweeper 20. At this time, the switching circuit 25 is repeatedly turned on and off by the modulation control circuit 26. The AC voltage applied to the chirped IDT 17 is therefore turned on and off, which modulates the surface elastic wave 15 or turns it on and off at a modulation frequency fr. A modulation frequency of about 100 kHz is selected with respect to fmin = 1.0 GHz and fmax = 2.0 GHz, which is a sufficiently low value in comparison with the frequency of the AC voltage applied to the chirped IDT 17. If the frequencies fmin, fmax are set to appropriate values when the frequency of the AC voltage, i.e., the frequency of the surface elastic wave 15, is swept, then the guided wave $L_1$ is diffracted most efficiently at the surface elastic wave frequency f (fmin $\leq$ f $\leq$ fmax) which meets equation (1) above. The light beam $L_4$ that is emitted from the optical waveguide 12 passes through the pinhole $30a$ and is detected by the light detector 31.

Since the surface elastic wave 15 is modulated or turned on and off, the light beam $L_4$ that is diffracted by the surface elastic wave 15 is also modulated at a modulation frequency fr. Therefore, the light intensity signal S1 produced by the light detector 31 is also modulated at a modulation frequency fr. A clock signal C, which has a frequency fr and is output by the modulation control circuit 26, is applied to the lock-in amplifier 35. A bandpass filter (not shown) in the lock-in amplifier 35 extracts a signal component having the same frequency as the frequency fr of the light intensity signal S1. The lock-in amplifier 35 then amplifies the extracted signal component, and issues the amplified signal component as a light intensity signal S1'. Generally, the light intensity signal S1 contains noise besides containing the signal component representative of the detected light beam $L_4$. However, this noise is filtered out by the bandpass filter in the lock-in amplifier 35, and hence the light-intensity signal S1' produced by the lock-in amplifier 35 has a high signal-to-noise ratio. Accordingly, the intensity of the diffracted light beam $L_4$ can be detected highly accurately.

The sampling circuit 32 connected to the sweeper 20 determines the frequency of the AC voltage when the Bragg conditions for diffraction are satisfied and the guided wave $L_1$ is diffracted, i.e., the frequency f of the surface elastic wave when the light intensity signal S1' generated by the lock-in amplifier 35 indicates a light intensity higher than a predetermined level. The sampling circuit 32 applies a signal S2, which represents the frequency f, to the control circuit 33, which stores therein the wavelength $\lambda$ref of the reference wave and the frequency fref of the reference surface elastic wave. On the basis of the wavelength $\lambda$ref, the frequency fref, and the surface elastic wave frequency f indicated by the signal S2, the control circuit 33 then calculates the wavelength $\lambda$ of the guided wave $L_1$ according to equation (3).

The control circuit 33 generates a signal S3 representing the wavelength $\lambda$ of the guided wave $L_1$ or the measured light beam, and applies the signal S3 to a display unit 34 which then displays the value of the wavelength $\lambda$. The display unit 34 may be a liquid crystal display unit, a photoelectric tube display unit, or the like.

The display unit 34 may be replaced with a suitable recording unit or the like. The wavelength $\lambda$ of the measured light beam need not necessarily be calculated by the control circuit 33 as in the above embodiment; it may be calculated manually. The wavelength $\lambda$ of the measured light beam can therefore be determined if the surface elastic wave frequency f is detected when the light detector 31 detects a light intensity higher than a predetermined intensity level.

Figure 4:
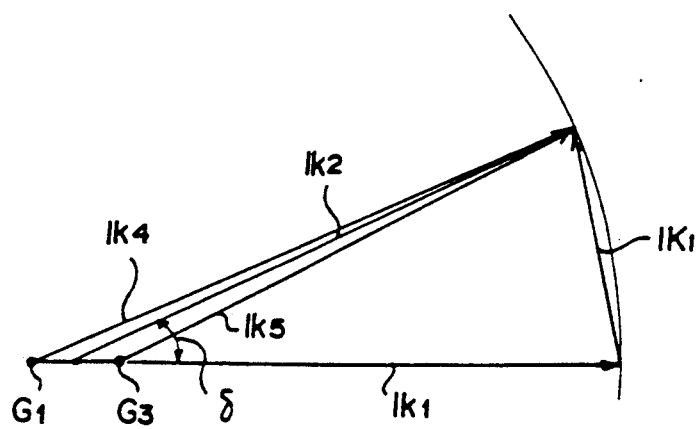
FIG. 4 is a diagram illustrating the manner in which an optical spectrum is separated in the optical spectrum analyzer shown in FIG. 1.

Even if a measured light beam is composed of plural spectral components having wavelengths lying very close to each other, the optical spectrum analyzer of the present invention can measure these spectral components with high resolution. This will be described in detail below. It is assumed that a measured light beam comprises spectral components having wavelengths $\lambda_1$, $\lambda_2$, $\lambda_3$ ($\lambda_1 < \lambda_2 \lambda_3$), which wavelengths have similar values. It is also assumed that, as shown in FIG. 4, the conditions for Bragg diffraction are met between a guided wave having the intermediate wavelength $\lambda_2$ and the surface elastic wave 15 and a diffracted light beam is emitted in the direction of the vector $k_2$. Then, guided waves having the wavelengths $\lambda_1$, $\lambda_3$ substantially, though not completely, satisfy the Bragg conditions for diffraction with respect to the surface elastic wave 15. Therefore, guided waves having the wavelengths $\lambda_1$, $\lambda_3$, are also diffracted by the surface elastic wave 15 and emitted from the optical waveguide 12. The angles through which these guided waves are diffracted are different from the angle through which a guided wave having the wavelength $\lambda_2$ is diffracted, and are indicated respectively by the angles between the vector $\mathbb{k}_1$ and vectors $\mathbb{k}_4$, $\mathbb{k}_5$ in FIG. 4 (the wave vectors of the guided waves having the wavelengths $\lambda_1$, $\lambda_3$ have respective starting points $G_1$, $G_3$). The light beams emitted from the optical waveguide 12 are therefore separated according to the respective spectral components they represent. If the spectral components are fully separated from each other on the pinhole plate 30, then when the frequency of the AC voltage is swept, three beams spots move on the pinhole plate 30 so that the light beams having the respective wavelengths successively pass through the pinhole 30a.

The intensities of the light beams detected by the light detector 31 and the AC voltage frequency or surface elastic wave frequency are related to each other as shown in FIG. 5. The spectral components having wavelengths $\lambda_1$, $\lambda_2$, $\lambda_3$ can individually be detected when the surface elastic wave frequencies are $f_1$, $f_2$, $f_3$, respectively. If the surface elastic wave frequencies $f_1$, $f_2$, $f_3$ are detected, then the wavelengths $\lambda_1$, $\lambda_2$, $\lambda_3$ can be determined in the same manner as described above.

Figure 7:
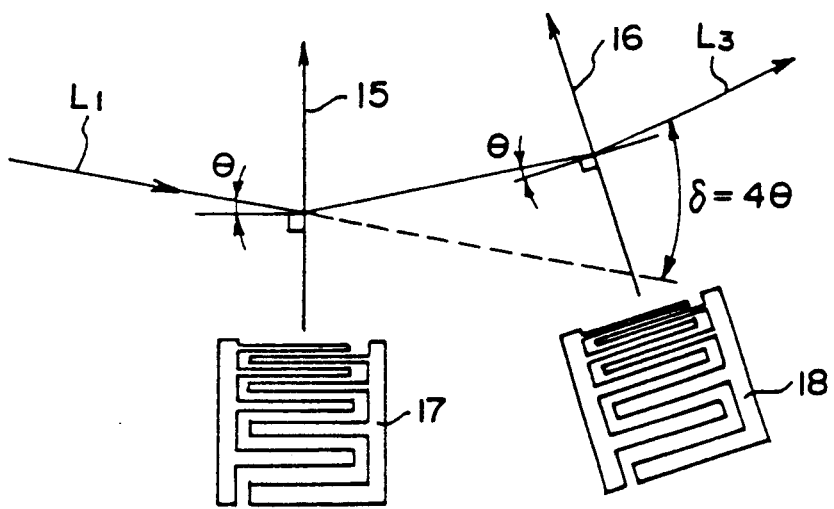
FIG. 7 is an enlarged plan view of a portion of the optical spectrum analyzer shown in FIG. 6.
Figure 8:
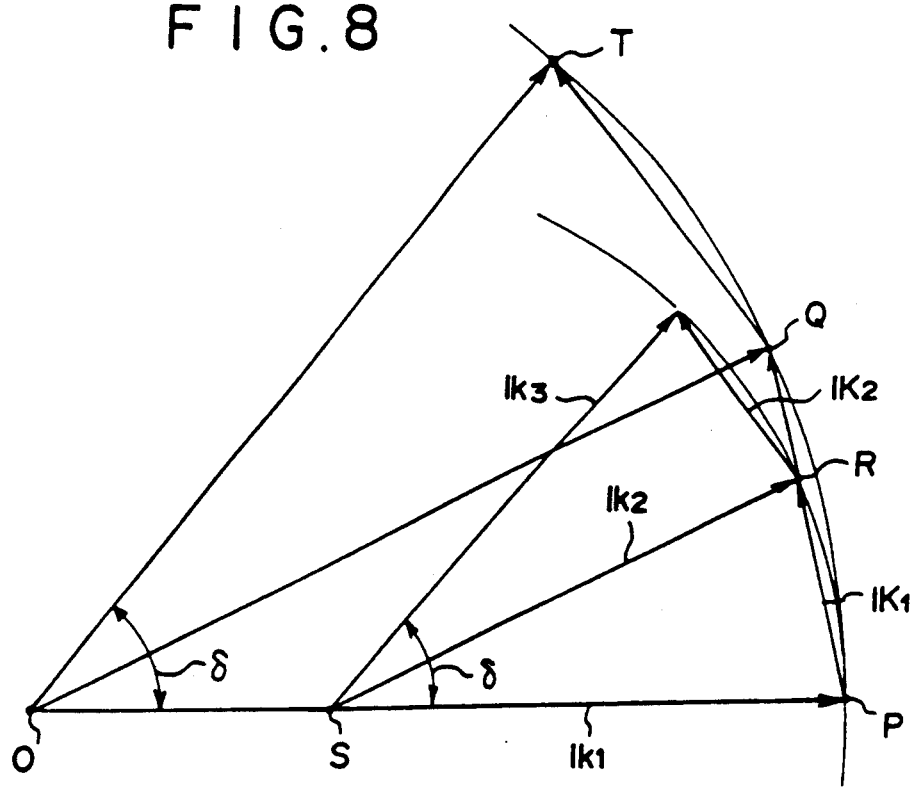
FIG. 8 is a diagram showing the manner in which a light beam is deflected in the optical spectrum analyzer shown in FIG. 6.

An optical spectrum analyzer according to a second embodiment of the present invention will be described below with reference to FIGS. 6, 7, and 8. Those parts of the optical spectrum analyzer shown in FIG. 6, 7, and 8 which are identical to those of the first embodiment are denoted by identical reference numerals, and will not be described in detail. As shown in FIGS. 6 and 7, an optical spectrum analyzer 50 includes, in addition to the chirped IDT 17, a second chirped IDT 18 disposed in the optical waveguide 12. The second chirped IDT 18 generates a second surface elastic wave 16 which further diffracts and deflects the guided wave $L_2$ in a direction that further amplifies the deflection of the guided wave $L_2$ diffracted by the first surface elastic wave 15. The high-frequency amplifier 19 applies an AC voltage having the same swept frequency to the first and second chirped IDTs 17, 18 so that the frequencies of the first and second surface elastic waves 15, 16 are of the same value and vary continuously. As with the first embodiment, the switching circuit 25 and the modulation control circuit 26 modulate or turn on and off the surface elastic waves 15, 16 at a modulation frequency fr which is sufficiently lower than the swept frequency of the AC voltage.

Let the wave vectors of a guided wave $L_1$, a guided wave $L_2$ diffracted by the first surface elastic wave 15, and a guided wave $L_3$ diffracted by the second surface elastic wave 16 be represented by $\mathbb{k}_1$, $\mathbb{k}_2$, $\mathbb{k}_3$, respectively, and also let the wave vectors of the first and second surface elastic waves 15, 16 be represented by $\mathbb{K}_1$, $\mathbb{K}_2$, respectively. Then, when the guided wave is diffracted twice as described above, the following equations are met:

$$\mathbb{k}_1 + \mathbb{K}_1 = \mathbb{k}_2$$

$$\mathbb{k}_2 + \mathbb{K}_2 = \mathbb{k}_3$$

If the chirped IDTs 17, 18 are arranged such that both the angle at which the guided wave $L_1$ is applied to the first surface elastic wave 15 and the angle at which the guided wave $L_2$ is applied to the second surface elastic wave 16 are $\downarrow$, then the wavelength $\lambda$ of the measured light beam L can be determined on the basis of the frequency f of the first and second surface elastic waves 15, 16, i.e., the frequency of the AC voltage applied to the IDTs 17, 18. Inasmuch as the light-intensity signal S1 produced by the light detector 31 is applied to the lock-in amplifier 35, the intensity of the light beam $L_4$ can be detected highly accurately with a high signal-to-noise ratio.

As with the first embodiment, use of a reference wave and first and second reference surfaces having the same frequency can determine the wavelength $\lambda$ of the measured light beam based on equation (3) above. More specifically, if the reference wave has a wave vector $\overrightarrow{OP}$, the first reference surface elastic wave a wave vector $\overrightarrow{PQ}$, the reference wave diffracted by the first reference surface elastic wave a wave vector $\overrightarrow{OQ}$, the second reference surface elastic wave a wave vector $\overrightarrow{QT}$, and the reference wave diffracted by the second reference surface elastic wave a wave vector $\overrightarrow{OT}$ in FIG. 8, then since $\triangle OPQ \sim \triangle SPR$, equation (3) is satisfied.

In the second embodiment, the angle $\delta$ through which the guided wave $L_3$ is deflected after it has been diffracted twice is $4\theta$ where $\theta$ is the angle of incidence of the guided wave $L_1$ with respect to the first surface elastic wave 15. This angle $\delta$ of deflection is twice as large as the angle $\delta$ of deflection ($\delta = 2\theta$) in the first embodiment. Accordingly, the resolution of spectrum analysis effected by the optical spectrum analyzer according to the second embodiment is higher than that of the optical spectrum analyzer according to the first embodiment. The higher resolution of the optical spectrum analyzer according to the second embodiment will be described in detail below.

In FIG. 4, for example, the angle formed between the vector $\mathbb{k}_2$ and the vector $\mathbb{k}_4$ or $\mathbb{k}_5$ becomes larger as the angle formed between the vector $\mathbb{k}_2$ and vector $\mathbb{k}_1$, i.e., the angle through which the guided wave is diffracted by the surface elastic wave, is larger. Therefore, the greater the angle $\delta$ of deflection of the guided wave, the larger the differences between the angles at which several light beams are simultaneously emitted from the optical waveguide 12, and hence the larger the distances at which the light beam spots are spaced on the pinhole plate 30. The greater angle $\delta$ of deflection of the guided wave allows spectral components having wavelengths which lie even closer to each other to be well separated from each other. As a result, the greater the angle $\delta$ of deflection, the higher the resolution of spectrum analysis carried out by the optical spectrum analyzer of the present invention.

A specific numerical example will be given below. When the guided wave is diffracted twice, since the angle $\delta$ of deflection is $4\theta$, it is expressed according to equation (1) as follows:

$$\delta = 4\sin^{-1}\frac{\lambda \cdot f}{2Ne \cdot v}$$

Thus, a change $\Delta\delta$ in the angle of deflection which occurs in response to a small change $\Delta\lambda$ in the wavelength is substantially give by:

$$\Delta\delta = 4\frac{\Delta\lambda \cdot f}{2Ne \cdot v}$$

It is assumed that the optical waveguide 12 is made of an X-cut crystal slab of LiNbO$_3$, Ne=2.2, v=3463 m/s, f =1.5 GHz, and the distance from the wave diffracting point to the pinhole plate 30 is l=90 mm. If the diameter of the light beam applied to the optical waveguide is D=15 mm, a beam spot having a diameter of 10 μm is formed on the pinhole plate 30. The distance at which two adjacent beam spots are spaced from each other on the pinhole plate 30 is approximately equal to l·Δδ, which is given by:

$$l·Δδ = 35,400 × Δδ$$

In the air, the distance is:

$$l·Δδ = 2.2 × 35,400 × Δδ = 77,800 × Δδ$$

If the spot-to-spot distance lΔδ is equal to at least the beam spot diameter, then two light beams can be detected separately. When the light beam L$_4$ is converged by the FGC 14 into a spot diameter of 10 μm which is equal to the diameter of the core of an optical fiber used in optical communications, for example, two light beams having wavelengths differing from each other by Δλ can be detected separately if $$77,880 × Δδ = 10 \ μm$$

From this equation, it can be determined that the wavelength difference Δλ is about 0.13 nm. Therefore, the optical spectrum analyzer according to the second embodiment can analyze an optical spectrum at a resolution represented by wavelength increments of about 0.1nm.

In cases where the optical spectrum analyzer is used to analyze the spectrum of a laser beam generated by a semiconductor laser, since the wavelength difference Δλ is normally a few nm, it is sufficient enough to assume that Δλ=100 nm. If the surface elastic wave frequency is about 1.5 GHz as described above, then the frequency band of the optical spectrum analyzer may be in the range of from 50 to 100 MHz.

While the frequencies of the first and second surface elastic waves 15, 16 are equal to each other at all times in the optical spectrum analyzer according to the second embodiment, these frequencies may be of different values but have a constant ratio.

The guided wave or the measured light beam may be diffracted three or more times by three or more surface elastic waves. As described above, the greater the angle δ of deflection of the guided wave, the higher the resolution of optical spectrum analysis. Consequently, if the guided wave is diffracted many times, the resolution of the optical spectrum analysis is increased, but it is not necessary to increase the frequencies of the surface elastic waves.

With the present invention, as described above, the optical spectrum analyzer can analyze optical spectrums with high resolution. Since the measured light beam is introduced into the optical waveguide and diffracted by a surface elastic wave or waves, the optical spectrum analyzer may be small in size and lightweight, and highly durable and reliable as it has no mechanical moving parts.

Modulating or turning on and off the surface elastic wave or waves also modulates or turns on and off the diffracted measured light beam, and a signal component having the same frequency as the modulation frequency is extracted from an output signal produced by a light detecting means, so that the measured light beam can be detected highly accurately and with a high signal-to-noise ratio. Accordingly, optical spectrum analysis can be effected with high precision by the optical spectrum analyzer according to the present invention. Because the measured light beam is modulated electrically, the optical spectrum analyzer of the invention remains smaller in size than conventional spectrum analyzers which employ mechanical choppers to modulate the measured light beam and which mutt be large in size in order for the measured light to be detected highly accurately and with a high signal-to-noise ratio.

Although certain preferred embodiments have been shown and described, it should be understood that many changes and modifications may be made therein without departing from the scope of the appended claims.

I claim:
1. An optical spectrum analyzer comprising:
   i) an optical waveguide made of a material capable of propagating a surface elastic wave therethrough;
   ii) surface elastic wave generating means for generating in said optical waveguide a surface elastic wave which has a continuously varying frequency and which diffracts and deflects a guided wave as it travels across the path of a guided wave, which guided wave is introduced as a measured light beam into and travels in said optical wave guide;
   iii) light detecting means for detecting said measured light beam which has been deflected by said surface elastic wave and emitted from said optical waveguide;
   iv) modulating means for turning on and off said surface elastic wave by repeatedly energizing and de-energizing said surface elastic wave generating means, the frequency of the modulation being lower than the continuously varying frequency;
   v) filter means for receiving a signal corresponding to said modulation frequency from said modulating means and a signal corresponding to said measured light beam from said light detecting means, and for extracting a signal component having the same frequency as said modulation frequency from said signal received from said light detecting means; and
   vi) frequency detecting means which is responsive to said signal component extracted by said filter means and detects the frequency of said surface elastic wave when said measured light beam is detected by said light detecting means.

2. An optical spectrum analyzer according to claim 1, wherein said light detecting means comprises a light detector and a pinhole plate disposed between said light detector and said optical waveguide, said pinhole plate having a pinhole for allowing said measured light beam to pass therethrough, which measured light beam has been emitted from said optical waveguide toward said light detector.

3. An optical spectrum analyzer according to claim 1, wherein said surface elastic wave generating means comprises a single chirped interdigital transducer for generating the surface elastic wave.

4. An optical spectrum analyzer according to claim 1, wherein said surface elastic wave generating means comprises a plurality of chirped interdigital transducers for generating respective surface elastic waves.

* * * * *